(12) United States Patent
Colesnic et al.

(10) Patent No.: US 12,195,417 B2
(45) Date of Patent: Jan. 14, 2025

(54) RHEOLOGY ADDITIVES BASED ON HYDROXYLATED DI-OR TRI-AMIDES AND MIXTURES THEROF

(71) Applicant: Arkema France, Colombes (FR)

(72) Inventors: Dmitri Colesnic, Paris (FR); Vincent Leroy, Verneuil en Halatte (FR); Laurent Lepinay, Verneuil en Halatte (FR)

(73) Assignee: Arkema France, Colombes (FR)

( * ) Notice: Subject to any disclaimer, the term of this patent is extended or adjusted under 35 U.S.C. 154(b) by 645 days.

(21) Appl. No.: 17/442,371

(22) PCT Filed: Mar. 27, 2020

(86) PCT No.: PCT/FR2020/000071
§ 371 (c)(1),
(2) Date: Sep. 23, 2021

(87) PCT Pub. No.: WO2020/201638
PCT Pub. Date: Oct. 8, 2020

(65) Prior Publication Data
US 2022/0185768 A1   Jun. 16, 2022

(30) Foreign Application Priority Data

Mar. 29, 2019 (FR) ................. FR19.03316

(51) Int. Cl.
*C07C 235/08* (2006.01)
*C09D 5/03* (2006.01)

(52) U.S. Cl.
CPC ............ *C07C 235/08* (2013.01); *C09D 5/037* (2013.01)

(58) Field of Classification Search
CPC ........ C07C 235/08; C09D 5/037; C09D 7/40; C08K 5/17; C08K 5/20; C08L 101/00; C08L 27/06; C08L 63/00; C08L 75/04; C08L 83/04
See application file for complete search history.

(56) References Cited

U.S. PATENT DOCUMENTS

2004/0261656 A1* 12/2004 Wu .................. C09D 11/34
                                              347/100
2015/0274644 A1* 10/2015 Bernard ............ C08K 5/20
                                              554/56
2016/0168079 A1   6/2016 Bernard
2016/0312005 A1  10/2016 Bernard et al.

FOREIGN PATENT DOCUMENTS

JP           61234919        10/1986

* cited by examiner

*Primary Examiner* — Yevgeny Valenrod
*Assistant Examiner* — Blaine G Doletski
(74) *Attorney, Agent, or Firm* — Debodhonyaa Sengupta

(57) ABSTRACT

The invention relates to a fatty amide which is a di- or triamide based on a polyether diamine or triamine which can be used as organogelator and in particular as rheology additive, said amide comprising a specific mixture of hydroxylated fatty acids and short hydroxylated acids. The invention also relates to a formulation composition using said fatty amide as rheology additive and to its use with this aim in coating, adhesive or PVC plastisol compositions and in particular transparent or non-transparent mastic compositions. Said rheology additive has the advantage of not needing a specific activation process before use, in contrast to the other known fatty amide additives based on hydrogenated castor oil derivatives.

17 Claims, No Drawings

RHEOLOGY ADDITIVES BASED ON HYDROXYLATED DI-OR TRI-AMIDES AND MIXTURES THEROF

CROSS-REFERENCE TO RELATED APPLICATIONS

This application is a national stage application under 35 U.S.C. § 371 of PCT/FR2020/000071, filed Mar. 27, 2020 which claims benefit to application FR19.03316, filed Mar. 29, 2019.

FIELD OF THE INVENTION

The present invention relates to a specific polyfunctional amide (di- and triamide) suitable for being used as organogelator, in particular as rheology additive and more particularly in coating compositions.

BACKGROUND OF THE INVENTION

EP 1 514 912 describes branched triamides of non-hydroxylated fatty acids based on polyether amines and used as phase-change vector agent in phase-change inks (known as "hot melt inks") with the function of causing the ink to pass from the solid state at ambient temperature to the liquid state at high temperature in inkjet printers and making it possible for the liquid ink droplets to solidify rapidly after they have been jetted at this temperature. EP 1 514 912 does not in the least suggest the use of these polyamides as organogelator agent or thixotropic agent and does not in the least suggest hydroxylated polyamides based on a mixture of hydroxylated fatty acids and shorter-chain hydroxylated monocarboxylic acids.

Fatty diamides based on aliphatic diamines (without polyether segments) and based on hydroxylated fatty acids are known as organogelator agents and in particular as thixotropic agents.

WO 2014/053774 describes hydroxylated fatty acid diamides as organogelator agent, or also known as rheology additive, in particular in coating, molding, mastic or leaktightness agent or cosmetic compositions.

WO 2015/011375 describes fatty acid diamines comprising, in their structure, both cycloaliphatic and aliphatic diamines with a specific molar ratio and the use of these products as organogelator agent or as rheology additive, in particular in coating, molding, mastic or leaktightness agent or cosmetic compositions.

FR 2 993 885 describes a fatty acid diamide comprising, in its structure, specific hydroxylated carboxylic acids and the use of this product as organogelator in coating, molding, mastic or leaktightness agent compositions.

These known diamides need to be micronized in the powder state and subsequently need an "activation" beforehand in order to give the required rheological performance qualities. The activation process requires a high-speed shearing and a heating sometimes ranging up to 100° C., depending on the products. Furthermore, a minimum period of time is required, which depends on the temperature conditions and on the polarity of the system. Moreover, these additives may not be very compatible with some binders for reactive formulations or with some diluents or plasticizers used for the activation. Consequently, this activation phase constitutes a particular disadvantage for polyamide powders and hydrogenated castor oil derivatives used as additives in this field.

There is thus a need for novel fatty polyamides which make possible simpler and easier shaping (shaping in the form of flakes readily soluble in the plasticizers or binders of final application reactive formulations, without the need for preactivation beforehand) with a broader spectrum of compatibility with the reactive binders and plasticizers/diluents used in reactive formulations, such as: silane-terminated polyether, silane-terminated polyurethane, polyurethane terminated by isocyanate, silicone, polysulfide, epoxy, and the like. The polyamides (meaning polyfunctional amides and not polymers) required as rheology additives must result in final products, in particular in coatings, mastic seals or sealing agent seals, which have an improved esthetic and surface appearance and which are transparent without surface defect, this being related to the specific structure and specific composition of these targeted polyamides.

The present invention, with novel fatty polyamides (polyfunctional fatty amides, in particular di- and triamides) based on primary polyamines (di- and triamines) comprising at least one polyether segment in its structure and in particular based on polyoxypropylene and based on fatty acids comprising at least one hydroxylated fatty acid in the presence of a shorter-chain hydroxylated acid, makes it possible to meet the new requirements defined above.

DETAILED DESCRPTION OF THE INVENTION

The first subject of the present invention therefore relates to a polyfunctional fatty amide which is a fatty diamide or triamide or a mixture thereof, based on a polyether polyamine (diamine or triamine) and on at least one saturated linear fatty acid bearing a non-terminal hydroxyl group in the presence of another shorter $C_2$-$C_{10}$ monocarboxylic acid bearing a hydroxyl group.

The second subject of the invention relates to a formulation composition of an organic binder, which composition comprises at least one organic binder and at least one fatty amide as defined according to the present invention, in particular as rheological additive.

The present invention also covers the use of at least one fatty amide as defined according to the present invention as rheology additive.

Finally, the invention also covers the final product obtained, which results from the use of at least one fatty amide as defined according to the present invention, as rheology additive, in particular as thixotropic agent.

Thus, the first subject of the present invention is a polyfunctional fatty amide, which is a diamide or a triamide or a mixture thereof, said fatty amide being represented by:
A) according to the following formula (I):

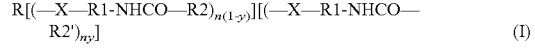

(I)

with
n being 2 or 3, preferably 3,
R(—X—R1-)$_n$ being the residue of valency n of a primary polyamine R(—X—R1-NH$_2$)$_n$ which is a primary diamine or triamine, with each primary amine group —NH$_2$ being a terminal group borne by a bivalent oligomer chain segment R1 chosen from polyether and polyester which is alkoxylated (alkoxylated polyester), preferably polyether and more preferentially polyoxypropylene or oxypropylene/oxyethylene copolymers having a predominance of oxypropylene units, R: $C_3$-$C_{10}$ alkylene residue of valency n resulting from a polyol R(OH)$_n$ or from a polyamine R(NH$_2$)$_n$ or R(NH—R3)$_n$, preferably from a polyol R(OH)$_n$, X: O, NH or NR3, preferably O, R2 being the $C_{12}$-$C_{52}$, preferably $C_{16}$-$C_{36}$, more preferentially $C_{16}$-$C_{24}$, fatty residue, without carboxyl group, of hydroxylated fatty acid R2CO$_2$H, in particular saturated and linear, R2' being the $C_2$ to $C_{10}$, preferably $C_2$ to $C_8$, more preferentially $C_2$ to $C_6$, monocarboxylic acid R2'CO$_2$H residue bearing at least one hydroxyl group, preferably at least two hydroxyl groups, with y representing the molar fraction of R2'CO$_2$H relative to the sum of R2CO$_2$H+R2'CO$_2$H (R2'/(R2+R2')), in said diamide, with y varying from 0.05 to 0.50, preferably from 0.10 to 0.40, with it being possible for R2CO$_2$H and/or R2'CO$_2$H to be mixtures of respective acids, R3 being a $C_1$-$C_2$ alkyl substituent, or (said fatty amide being represented) by:

B) according to the following formula (II) in the case in which said amide is a diamide:

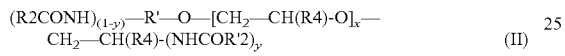
(II)

with R' being the residue of monopropylene glycol without OH: —CH(CH$_3$)—CH$_2$— and x being the number of oxyalkylene units —CH$_2$—CH(R4)-O— and it being possible for x to vary from 5 to 45, preferably from 5 to 40 and more preferentially from 5 to 35. R2 and R'2 and "y" being defined as in formula (I) above and R4 being H or methyl with the repeating oxyalkylene unit —CH$_2$—CH(R4)-O— being ethoxy when R4 is H and propoxy when R4 is methyl or R4 corresponds to an ethoxy/propoxy mixture and preferably R4 is methyl with said oxyalkylene unit being propoxy, and said amide having a melting point, meaning melting temperature, measured by DSC after two passes, 10° C./min, ranging from 10 to 110° C., preferably from 20 to 100° C.

The term "melting point" corresponds to the melting temperature measured by differential scanning calorimetry (DSC) at a heating rate of 10° C./min. This temperature is the temperature which corresponds to the melting peak recorded by DSC at the specified heating rate.

Regarding the residue R, said $C_3$-$C_{10}$ alkylene, in addition to the carbon-carbon bonds, may comprise an ether bridge —O— in the case of a polyol residue or an —NH— bridge in the case of a polyamine residue.

In the case in which X: N, as appears clearly from the formulae specified above for polyamines containing R residue, this means that N represents —NH— and —N(R3)-.

Regarding the meaning of R2CO$_2$H, this relates to linear hydroxylated fatty acids with non-terminal hydroxyl. These linear fatty acids contain a linear $C_{12}$-$C_{52}$, preferably $C_{16}$-$C_{36}$, more preferentially $C_{16}$-$C_{24}$, fatty chain, in particular consisting exclusively of C—C bonds and therefore without ester groups within this linear chain. This definition therefore excludes from the definition of R2CO$_2$H any polyester or oligoester obtained from the self-polycondensation of a hydroxylated fatty acid.

In the case of monocarboxylic acids R2'CO$_2$H, the term "$C_2$-$C_{10}$, preferably $C_2$-$C_8$, more preferentially $C_2$—$O_6$" means that this is the length of the chain of R2' expressed as the number of chained carbon atoms (—C—C—), without taking into account side substituents.

According to a specific option, the acid R2CO$_2$H is a mixture of hydroxylated fatty acids and/or the acid R2'CO$_2$H is a mixture of shorter-chain (compared to the hydroxylated fatty acids) hydroxylated monocarboxylic acids as defined according to the invention. As suitable examples of primary polyamines corresponding to the formula R(—X—R1-NH$_2$)$_n$, which are primary diamines or triamines as defined above, mention may be made of the following:

as diamine (n=2) or triamine (n=3): a primary diamine with the two primary amine functional groups borne by a polyether segment or an alkoxylated polyester (polyester-polyether) segment or a triamine with 3 primary amine functional groups borne by 3 polyether or alkoxylated polyester (polyester-polyether) segments, said polyether or alkoxylated polyester segment for a diamine, or the combination of the 3 polyether or alkoxylated polyester segments in the case of a triamine, having a number-average molecular weight Mn ranging from 500 to 3000. In particular, they are primary diamine and triamine polyethers and more particularly primary diamine and triamine polyoxypropylenes, such as the Jeffamine® diamines and triamines sold by Huntsman with as more specific suitable examples Jeffamine® D-2000 (primary diamine with a polyoxypropylene segment bearing 2 primary amine groups with a number of oxypropylene units of 33) or Jeffamine® T-3000 (primary triamine with 3 polyoxypropylene segments and a total number of oxypropylene units of 50). Other amines can also be used: Jeffamine® D-400, Jeffamine® D-2010, Jeffamine® 1-403, Jeffamine® T-5000, and the like.

In principle, said polyether diamines or polyether triamines suitable for preparing the diamides and triamides according to the present invention may be obtained from corresponding polyether polyol (respectively diol or triol) precursors by reductive amination of the terminal OH functions in the presence of a catalyst, as described in U.S. Pat. No. 4,766,245 or GB 2175910.

Regarding the respective polyether polyol (diol or triol) precursors of polyether diamines or triamines, they may be obtained by anionic polymerization in basic medium of the corresponding alkylene oxide (ethylene oxide for polyoxyethylene diol/triol, propylene oxide for polyoxypropylene diol/triol) or a mixture of said alkylene oxides in the presence of a polyol alkoxide initiator with primary OH groups, which is respectively diol or triol (with primary OH groups), or a polyamine initiator, respectively diamine and triamine (according to the functionality of said polyether: diol or triol). As example of diol initiator, mention may be made of ethylene glycol, diethylene glycol, 1,3-propylene glycol, 1,4-butylene glycol. As example of triol initiator, mention may be made of trimethylolpropane.

In the case of bivalent initiators (two primary alkoxide functions or two amine functions), they lead to a symmetrical structure with the initiator incorporated in the middle of the chain (via ether —O— or —NH— bond) and with the start of a polyether chain for each alkoxide or amine function of the initiator used.

In the case of a trivalent initiator (primary alkoxide triol or triamine), each alkoxide or amine is the starting point for a polyether chain, with the result being 3 polyether chains borne by a molecule of said initiator, the residue of which corresponds to R in the formula defined above for the amide according to the invention.

In the particular case of polyether diamines, the polyether diol precursors may also be obtained by anionic polymerization of the alkylene oxide or of a corresponding mixture of alkylene oxides (for example ethylene oxide or propylene oxide or a mixture of ethylene oxide and propylene oxide for, respectively, polyoxyethylene diols, polyoxypropylene diols and (oxyethylene-oxypropylene) diol copolymers) from a monovalent primary alkoxide initiator bearing an OH on a secondary carbon of said initiator (which secondary OH does not react to open the alkylene oxide). In such a case, a single polyether chain is formed from the primary alkoxide, the other (secondary) OH portion of the initiator remaining free and unchanged and thus, with the polyether formed, being a diol (polyether diamine precursor by conversion of the terminal OH groups to NH2 as mentioned above). An example of monovalent diol initiator (1 single primary OH) is monopropylene glycol in the primary alkoxide form, as below:

HO—CH(CH$_3$)—CH$_2$O

In the more particular case of polyether diamines based on polyoxypropylene, the monopropylene glycol acts as monovalent initiator, with secondary hydroxyl being unaffected during the polymerization of the propylene oxide (ring-opening initiation by attack of the anionic alkoxide initiator on the least electron-rich carbon atom (—CH$_2$—) of the propylene oxide and subsequent chain propagation), leading to the polyoxypropylene diol of the following formula, which bears two secondary OH groups:

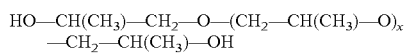

HO—CH(CH$_3$)—CH$_2$—O—(CH$_2$—CH(CH$_3$)—O)$_x$
—CH$_2$—CH(CH$_3$)—OH

After conversion of the terminal secondary hydroxyls (by catalyzed reductive amination under NH$_3$ pressure as described in U.S. Pat. No. 4,766,245 or GB2175910), the polyoxypropylene diamine of following formula may be obtained:

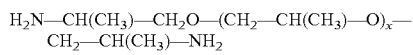

H$_2$N—CH(CH$_3$)—CH$_2$O—(CH$_2$—CH(CH$_3$)—O)$_x$—
CH$_2$—CH(CH$_3$)—NH$_2$

As an example of such a polyoxypropylene diamine, mention may be made of Jeffamine® D2000, sold by Huntsman.

Use may be made, as hydroxylated saturated linear fatty acids R2CO$_2$H (with R2 bearing a non-terminal OH) as defined according to the invention, of a hydroxy fatty acid chosen from 12-hydroxystearic acid (12-HSA), 9-hydroxystearic acid (9-HSA), 10-hydroxystearic acid (10-HSA), 14-hydroxyeicosanoic acid (14-HEA), or mixtures thereof.

As shorter C$_2$-C$_{10}$ acids R2'CO2H, it is possible to use 2,2-bis(hydroxymethyl)propionic acid, 2,2-bis(hydroxymethyl)butyric acid, hydroxyacetic acid (or glycolic acid), 2-hydroxypropionic acid (lactic acid), 2-hydroxy-3-(3-pyridyl)propionic acid, 3-hydroxybutyric acid, 2-hydroxybutyric acid, 2-methyl-2-hydroxybutyric acid, 2-ethyl-2-hydroxybutyric acid, hydroxypentanoic acid, hydroxyhexanoic acid, hydroxyheptanoic acid, hydroxyoctanoic acid, hydroxynonanoic acid, hydroxydecanoic acid and mixtures thereof; preferably 2,2-bis(hydroxymethyl)propionic acid, 2,2-bis(hydroxymethyl)butyric acid, hydroxyacetic acid (or glycolic acid), 2-hydroxypropionic acid (lactic acid), 2-hydroxy-3-(3-pyridyl)propionic acid, 3-hydroxybutyric acid, 2-hydroxybutyric acid, 2-methyl-2-hydroxybutyric acid, 2-ethyl-2-hydroxybutyric acid, hydroxypentanoic acid, hydroxyhexanoic acid, hydroxyheptanoic acid, hydroxyoctanoic acid and mixtures thereof; more preferentially 2,2-bis(hydroxymethyl)propionic acid, 2,2-bis(hydroxymethyl)butyric acid, hydroxyacetic acid (or glycolic acid), 2-hydroxypropionic acid (lactic acid), 2-hydroxy-3-(3-pyridyl)propionic acid, 3-hydroxybutyric acid, 2-hydroxybutyric acid, 2-methyl-2-hydroxybutyric acid, 2-ethyl-2-hydroxybutyric acid, hydroxypentanoic acid, hydroxyhexanoic acid, and mixtures thereof.

The fatty amide according to the invention represented by A according to formula (I) preferably has a number-average molecular weight Mn, measured by GPC in THF as polystyrene equivalents (calibration by polystyrene standards) which varies for:
  n=2 (a diamide) from 800 to 4000, preferably from 1000 to 3800,
  n=3 (a triamide) from 1000 to 6000, preferably from 2000 to 5500.

The fatty amide according to the invention represented by B according to formula (II) which is a fatty diamide preferably has the same range of number-average molecular weight Mn, measured by GPC in THF as polystyrene equivalents (calibration by polystyrene standards), as the diamide (n=2) represented by option A) according to formula (I), that is to say: from 800 to 4000, preferably from 1000 to 3800.

According to a preferred option for the fatty amide represented by option A) according to formula (I), said oligomer chain segment R1 is a polyether chain segment.

According to a more particularly preferred option, said oligomer chain segment R1 is a polyoxypropylene chain segment.

Said oligomer chain segment R1 can have a number-average molecular weight Mn ranging from 400 to 2000, preferably from 500 to 1500.

According to a specific option of the invention, said fatty amide is a fatty diamide represented by option B) according to formula (II) as defined above.

According to a preferred option, said hydroxylated fatty acid R2CO$_2$H is selected from 12-hydroxystearic acid (12-HSA); 9- or 10-hydroxystearic acid (9-HSA or 10-HSA), preferably a mixture of 9- and 10-hydroxystearic acids; 14-hydroxyeicosanoic acid (14-HEA), and mixtures thereof in pairs. The most preferred hydroxylated acid R2CO$_2$H is 12-hydroxystearic acid.

More particularly preferably, said monocarboxylic acid R2'CO$_2$H is selected from: 2,2-bis(hydroxymethyl)propionic acid, 2,2-bis(hydroxymethyl)butyric acid, hydroxyacetic acid (or glycolic acid), 2-hydroxypropionic acid (lactic acid), 2-hydroxy-3-(3-pyridyl)propionic acid, 3-hydroxybutyric acid, 2-hydroxybutyric acid, 2-methyl-2-hydroxybutyric acid, and 2-ethyl-2-hydroxybutyric acid.

According to another specific option of the invention, said amide is a diamide according to A) or B) or a triamide according to A), with the ratio "y/(1−y)" varying from 1/20 to 1/2 and preferably from 1/10 to 4/10.

According to another alternative option, said amide is a diamide according to A) or B), with the ratio y/(1−y) varying from 1/10 to 1/2 and preferably from 1/10 to 4/10.

According to a specific option, said amide is a triamide according to A) with two residues (R2) resulting from hydroxylated fatty acid R2CO$_2$H and one (R2') resulting from acid R2'CO$_2$H.

More particularly and as an alternative, said amide is a diamide represented according to option A) and represented by formula (I) or according to option B) and represented by formula (II) as are defined above.

The second subject of the invention relates to a formulation composition of an organic binder, characterized in that it comprises:
a) at least one organic binder and
b) at least one fatty amide as defined above according to the invention, in particular as rheological additive.

More particularly, in said binder formulation composition, said binder a) is selected from: polysiloxane resins terminated by blocked silane groups, polyether resins terminated by blocked silane groups, polysulfide resins terminated by blocked silane groups, polyurethane prepolymer resins terminated by isocyanate groups, PVC resins for plastisols, epoxy resins bearing epoxy groups.

Said composition can comprise, in addition to a) and b) and depending on said binder, a plasticizer or a reactive diluent as defined below:

c) a plasticizer for polysiloxane resins, polyurethane prepolymer resins and PVC resins for plastisols or
d) a reactive diluent from epoxidized monomers for epoxy resins and optionally
e) for two-component systems, a hardener for the epoxy or polyurethane resins.

More particularly, in said composition according to the invention, said fatty amide is used as rheological additive which is a thixotropic agent.

In said composition, said organic binder a) can be selected from a polysiloxane resin, a polyurethane prepolymer resin or a PVC resin for plastisols and said plasticizer can be selected from: phthalates, adipates, trimellitates, sebacates, benzoates, citrates, phosphates, epoxides, polyesters, alkylsulfonate esters and non-phthalate substitutes for phthalates.

According to a specific option, said composition is a transparent or non-transparent mastic formulation composition. According to a more specific option, it is a transparent mastic formulation composition.

Another subject of the invention covers the use of at least one fatty amide as defined above according to the invention where said amide is used as rheology additive.

In said use, said rheology additive can be used as thixotropic agent.

More particularly, said use can be in coating, adhesive, PVC plastisol or mastic compositions, preferably PVC plastisol compositions and mastic compositions.

Another specific use is in PVC plastisol compositions.

Another specific use is in mastic compositions which can be crosslinked by moisture based on polysiloxane resins terminated by blocked silane groups, polyether resins terminated by blocked silane groups, polysulfide resins terminated by blocked silane groups, in particular silanes blocked by alkoxy groups, or polyurethane prepolymer resins terminated by isocyanate groups.

Another specific use is in mastic compositions which can be crosslinked by moisture, which mastics are or are not transparent.

Finally, the invention covers a final product which can be a coating, in particular PVC plastisol coating, or an adhesive seal or a mastic seal, which results from the use of at least one fatty amide as defined above according to the invention, as rheology additive, in particular as thixotropic agent.

The following examples of the experimental section below are presented by way of illustration of the invention and of its performance qualities and do not in any way limit its scope.

EXPERIMENTAL SECTION

1) Starting Materials Used and Codes
See Table 1 below
Table summarizing the starting materials used in synthesis and in formulations

TABLE 1

| Product used | Chemical name | Function | Supplier |
| --- | --- | --- | --- |
| 12HSA | 12-Hydroxystearic acid | Hydroxylated fatty acid | Jayant Agro |
| Stearine | Stearic acid | Non-hydroxylated fatty acid, according to R2CO$_2$H | Sogis |
| bMBA | 2,2-bis(hydroxymethyl) butyric acid | Short hydroxylated acid according to R2'CO$_2$H | Sigma Aldrich |
| JEFFAMINE ® T-3000 Polyetheramine | Jeffamine ® T-3000 polyetheramine | Polyoxypropylene triamine (primary) with overall ~50 oxypropylene (OP) units | Huntsman |
| JEFFAMINE ® D-2000 Polyetheramine | Jeffamine ® D-2000 polyetheramine | Polyoxypropylene diamine (primary) with ~33 OP units | Huntsman |
| HCO (as flakes) | Hydrogenated castor oil | Reference rheology additive | Gokul Agro |
| Crayvallac ® Antisettle CVP (micronized powder) | Hydrogenated castor oil | Reference rheology additive | Arkema |
| Standard fatty diamide | 12HSA—HMDA—12HSA | Reference diamide rheology additive for comparison | / |
| MS Polymer ® S203H | Silylated polyether | Applicative formulation resin | Kaneka |
| Jayflex ® DIUP | Diisoundecyl phthalate | Plasticizer for formulation | BASF |

For reasons of clarity, the following abbreviations will be used:
- 12HSA: 12-Hydroxystearic acid
- SA: Stearic acid
- HMDA: Hexamethylenediamine
- D2000: Jeffamine® D-2000 polyetheramine
- T3000: Jeffamine® T-3000 polyetheramine
- bMBA: 2,2-bis(hydroxymethyl)butyric acid 2) Examples Example A According to the Invention—T3000-(12HSA-bMBA)$_3$ 231.40 g of Jeffamine® T-3000 (0.078 mol, 1 eq), 63.11 g of 12-hydroxystearic acid (0.199 mol, 2.55 eq) and 5.2 g of 2,2-bis(hydroxymethyl)butyric acid (0.035 mol, 0.45 eq) are added to a 1 liter round-bottom flask equipped with a thermometer, a Dean-Stark apparatus, a condenser and a stirrer. The mixture is heated to 180° C. under an inert atmosphere. The water removed accumulates in the Dean-Stark apparatus from 150° C. The reaction is monitored by the acid number and the amine number. When the acid and amine numbers are respectively less than 6, the reaction is halted. The reaction mixture is cooled to 140° C. and is discharged into a silicone mold. Once cooled to ambient temperature, the product is converted into flakes.

Example B According to the Invention—D2000-(12HSA-bMBA)$_2$ 232.3 g of Jeffamine® D-2000 (0.115 mol, 1 eq), 62.12 g of 12-hydroxystearic acid (0.196 mol, 1.7 eq) and 5.11 g of 2,2-bis(hydroxymethyl)butyric acid (0.034 mol, 0.3 eq) are added to a 1 liter round-bottom flask equipped with a thermometer, a Dean-Stark apparatus, a condenser and a stirrer. The mixture is heated to 180° C. under an inert atmosphere. The water removed accumulates in the Dean-Stark apparatus from 150° C. The reaction is monitored by the acid number and the amine number. When the acid and amine numbers are respectively less than 6, the reaction is halted. The reaction mixture is cooled to 140° C. and is discharged into a silicone mold. Once cooled to ambient temperature, the product is converted into flakes.

Comparative Example C—T3000-(SA)$_3$ 313.6 g of Jeffamine® T-3000 (0.10 mol, 1 eq) and 86.4 g of stearic acid (0.3 mol, 3 eq) are added to a 1 liter round-bottom flask equipped with a thermometer, a Dean-Stark apparatus, a condenser and a stirrer. The mixture is heated to 180° C. under an inert atmosphere. The water removed accumulates in the Dean-Stark apparatus from 150° C. The reaction is monitored by the acid number and the amine number. When the acid and amine numbers are respectively less than 6, the reaction is halted. The reaction mixture is cooled to 140° C. and is discharged into a silicone mold.

Comparative Example D—D2000-(SA)$_2$ 312.2 g of Jeffamine® D-2000 (0.15 mol, 1 eq) and 87.8 g of stearic acid (0.3 mol, 2 eq) are added to a 1 liter round-bottom flask equipped with a thermometer, a Dean-Stark apparatus, a condenser and a stirrer. The mixture is heated to 180° C. under an inert atmosphere. The water removed accumulates in the Dean-Stark apparatus from 150° C. The reaction is monitored by the acid number and the amine number. When the acid and amine numbers are respectively less than 6, the reaction is halted. The reaction mixture is cooled to 140° C. and is discharged into a silicone mold.

3) Study of the Gelling Power of the Organogelators

In this study, the ability of the tested rheology additives to form a gel in a simplified formulation containing solely a conventional plasticizer (Jayflex® DIUP) used in PVC plastisol formulations will be compared.

The formulations are prepared using a laboratory "planetary" mixer (Molteni® EMD 1 type) provided with a dispersing disk and a scraper which makes it possible to mix high-viscosity products but also powders in non-fluid systems. It is equipped with a vacuum pump which makes it possible to prevent the ingress of moisture during the dispersing. The temperature within the Molteni® EMD 1 is recorded by a probe attached to the scraper and can be regulated by virtue of a bath.

The simplified formulations tested/compared are presented in table 2 below with the common plasticizer being Jayflex® DIUP and the variable rheology additive tested and compared being the amides mentioned or other reference products mentioned.

Composition of the Simplified Formulations

TABLE 2

| Formulation | Component | Weight % |
|---|---|---|
| F1 | Jayflex ® DIUP plasticizer | 95 |
|  | Example A amide | 5 |
| F2 | Jayflex ® DIUP plasticizer | 95 |
|  | Example B amide | 5 |
| F3 | Jayflex ® DIUP plasticizer | 95 |
|  | Example C amide | 5 |
| F4 | Jayflex ® DIUP plasticizer | 95 |
|  | Example D amide | 5 |
| F5 | Jayflex ® DIUP plasticizer | 95 |
|  | 12HSA-HMDA-12HSA | 5 |
| F6 | Jayflex ® DIUP plasticizer | 95 |
|  | HCO | 5 |
| F7 | Jayflex ® DIUP plasticizer | 95 |
|  | Crayvallac ® Antisettle CVP | 5 |

The rheology additive is introduced into the plasticizer and the mixture is brought to the incorporation temperature (cf. table 3) and dispersed for 5 minutes. At the end of the dispersing, the mixture is cooled to ambient temperature and the behavior of the gel is studied visually (see table 3 below).

Behavior and Appearance of the Gel as a Function of the Incorporation Temperature

TABLE 3

| Formulation | Temperature | Behavior of the gel | Appearance |
|---|---|---|---|
| F1 | 60° C.** | Strong gel | Transparent |
|  | 80° C.** | Strong gel | Transparent |
| F2 | 60° C.** | Strong gel | Transparent |
|  | 80° C.** | Strong gel | Transparent |
| F3 | 60° C.** | Liquid | Transparent |
|  | 80° C.** | Liquid | Transparent |
| F4 | 60° C.** | Liquid | Transparent |
|  | 80° C.** | Liquid | Transparent |
| F5 | 60° C.* | Weak gel | Opaque |
|  | 80° C.* | Weak gel | Opaque |
|  | 100° C.** | Weak gel | Opaque |

TABLE 3-continued

| Formulation | Temperature | Behavior of the gel | Appearance |
|---|---|---|---|
| F6 | 60° C.* | Weak gel (presence of grains) | Opaque |
|  | 80° C.** | Weak gel | Opaque |
| F7 | 60° C.* | Strong gel | Opaque |
|  | 80° C.** | Weak gel (slight syneresis) | Opaque |

*partial dissolution; **complete dissolution

The results of the gel tests show that the products according to the invention (amides according to examples A and B) form gels, while the comparative products are in the liquid form. Thus, the compound of example C described in particular in EP 1 514 912 A2 does not make it possible to obtain the gel (cf. formulation F3), which strongly indicates that the presence of the hydroxyl group, providing H bonds, is essential to the formation of the supramolecular assembly and of the three-dimensional (3D) network of fibers formed.

The behavior of the organogelator agents can also be influenced by the initial structure of the amine used. Thus, on comparing the organogelator described in WO 2014/053774A1 (12HSA-HMDA-12HSA) with the compound of example B according to the invention, a significant difference in gel strength may be observed. In particular, if the aliphatic amine is replaced with a polyether amine, the gelling power increases, making it possible, in addition, to obtain a transparent gel. It should be noted that, in order to be completely dissolved, the compound 12HSA-HMDA-12HSA (cf. formulation F5) requires greater temperatures than the products according to the invention.

Furthermore, the performance qualities of the gels can be linked to the physical nature of the rheology additive. Consequently, for formulations F6 and F7 to begin with at a constant temperature (60° C.) of incorporation of the rheology additive, a difference in gel strength is observed. Namely, if the additive is in the form of flakes (cf. formulation F5), the gel strength will decrease, which might well be explained by an incomplete incorporation of the product in the formulation due to the lack of solubility. Furthermore, grains could be observed, which might corroborate this hypothesis.

Also, it may be observed that, in the case where the additive is in the powder form and is incorporated at a higher temperature (80° C. in F7) than its optimum incorporation temperature (60° C. in F7), the gel strength will decrease, which shows in addition a sensitivity to the temperature due probably to the over-dissolution of the product. It is thus important, in the case of the standard products, to indeed observe an incorporation temperature window for which the organogelator is effective.

As regards formulations F1 and F2 containing the products according to the invention, the formation of a strong gel may be observed irrespective of the incorporation temperature. It should be mentioned that, at the temperatures studied, the rheology additive is completely dissolved. Furthermore, the formulations exhibit a completely transparent appearance.

4) Evaluation of the Rheological Performance Qualities in a Simplified Hybrid Mastic Formulation This study compares the rheological performance qualities of the additives of a simplified hybrid mastic formulation comprising, as plasticizer: Jayflex® DIUP and, as rheology additive, the mentioned product being compared.

Composition of the Simplified Hybrid Mastic Formulations

TABLE 4

| Formulation | Component | % by weight | Function |
|---|---|---|---|
| F8 | Jayflex ® DIUP plasticizer | 47.5 | Plasticizer |
|  | MS-Polymer ® S 203 H | 47.5 | Resin |
|  | Amide according to example A | 5 | Rheology additive |
| F9 | Jayflex ® DIUP plasticizer | 47.5 | Plasticizer |
|  | MS-Polymer ® S 203 H | 47.5 | Resin |
|  | Crayvallac Antisettle CVP | 5 | Rheology additive |
| F10 | Jayflex ® DIUP plasticizer | 47.5 | Plasticizer |
|  | MS-Polymer ® S 203 H | 47.5 | Resin |
|  | Amide according to example B | 5 | Rheology additive |
| F11 | Jayflex ® DIUP plasticizer | 47.5 | Plasticizer |
|  | MS-Polymer ® S 203 H | 47.5 | Resin |
|  | 12HSA—HMDA—12HSA | 5 | Rheology additive |

The formulations are prepared using a Molteni® EMD 1 mixer. The resin and the plasticizer are added and homogenized in a first stage and in the proportions shown (table 4). The additive is weighed out and subsequently added during the second stage. Thus, the reaction mixture, which is kept under vacuum during the mixing phases, is brought to 80° C. for 5 minutes. At the end of this phase, the mixture is cooled to 25° C. and discharged. The performance qualities of these formulations are presented in table 5 below.

Rheological Performance Qualities

TABLE 5

| Formulation | Viscosity at 0.1 s$^{-1}$ (Pa·s) | Viscosity at 100 s$^{-1}$ (Pa·s) | Thixotropic index | Yield stress (Pa) | Appearance |
|---|---|---|---|---|---|
| F8 | 717 | 3.50 | 205 | 73 | Transparent |
| F9 | 296 | 6.06 | 49 | 4.4 | Opaque |
| F10 | 313 | 2.78 | 113 | 30 | Transparent |
| F11 | 47 | 2.21 | 21 | 3.1 | Opaque |

The triamide rheology additive of example A according to the invention proves to be much more effective in terms of rheological performance qualities (cf. formulation F8), compared with the standard powder additive Crayvallac® Antisettle CVP (cf. formulation F9). With regard to the diamide product of example C, it also exhibits rheological performance qualities (cf. formulation F10) which are superior to that using the compound in the powder form 12HSA-HMDA-12HSA (cf. formulation F11).

Furthermore, the products according to the invention do not need a specific processing process to develop the rheology (gel), as is necessary in the case for conventional additives in the form of powders based on hydrogenated castor oil derivatives.

Furthermore, as the products according to the invention are in the form of flakes, problems encountered with the use of powders (micronization, handling, toxicity, and the like) are thus eliminated. It should also be noted that these products make it possible to obtain MS mastic formulations which are completely transparent.

The invention claimed is:

1. A polyfunctional fatty amide which is a diamide, a triamide or a mixture thereof, wherein said polyfunctional fatty amide is represented by:
A) formula (I):

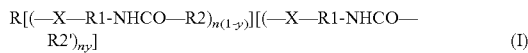

(I)

with
n being 2 or 3, preferably 3,
R(—X—R1-)$_n$ being the residue of valency n of a primary polyamine R(—X—R1-NH$_2$)$_n$ which is a primary diamine or triamine,
with each primary amine group —NH$_2$ being a terminal group borne by a bivalent oligomer chain segment R1 chosen from alkoxylated polyester and polyether,
R: $C_3$-$C_{10}$ alkylene residue of valency n resulting from a polyol R(OH)$_n$ or from a polyamine R(NH$_2$)$_n$ or R(NH—R3)$_n$,
X: O, NH or NR3,
R2 being the $C_{12}$-$C_{52}$, fatty residue of hydroxylated fatty acid R2CO$_2$H,
R2' being the $C_2$ to $C_{10}$ monocarboxylic acid R2'CO$_2$H residue bearing at least one hydroxyl group,
y representing the mean molar fraction of R2'CO$_2$H relative to the sum of R2CO$_2$H+R2'CO$_2$H, in said diamide, with y varying from 0.05 to 0.50, with R2CO$_2$H and/or R2'CO$_2$H optionally being mixtures of respective acids,
R3 being a $C_1$-$C_2$ alkyl substituent,
and said amide having a melting point, meaning melting temperature, measured by differential scanning calorimetry (DSC) after two passes at 10° C./min, ranging from 10 to 110° C.

2. The fatty amide as claimed in claim 1, wherein a number-average molecular weight Mn of said fatty amide defined according to A) formula (I), measured by gel permeation chromatography (GPC) in tetrahydrofuran (THF) as polystyrene equivalents varies for:
n=2 from 800 to 4000,
n=3 from 1000 to 6000.

3. The fatty amide as claimed in claim 1 wherein said oligomer chain segment R1 for the fatty amide according to A) formula (I) is a polyether chain segment.

4. The fatty amide as claimed in claim 1 wherein said oligomer chain segment R1 is a polyoxypropylene chain segment.

5. The fatty amide as claimed in claim 1 wherein said oligomer chain segment R1 has a number-average molecular weight Mn ranging from 400 to 2000.

6. The fatty amide as claimed in claim 1 wherein said hydroxylated fatty acid R2CO$_2$H is selected from 12-hydroxystearic acid (12-HSA); 9-hydroxystearic acid (9-HAS), 10-hydroxystearic acid (10-HSA), a mixture of 9-and 10-hydroxystearic acids; 14-hydroxyeicosanoic acid (14-HEA); and mixtures thereof.

7. The fatty amide as claimed in claim 1 wherein said hydroxylated fatty acid R2CO$_2$H is 12-hydroxystearic acid.

8. The fatty amide as claimed in claim 1 wherein said monocarboxylic acid R2'CO$_2$H is selected from: 2,2-bis (hydroxymethyl)propionic acid, 2,2-bis (hydroxymethyl) butyric acid, hydroxyacetic acid (or glycolic acid), 2-hydroxypropionic acid (lactic acid), 2-hydroxy-3-(3-pyridyl) propionic acid, 3-hydroxybutyric acid, 2-hydroxybutyric acid, 2-methyl-2-hydroxybutyric acid, 2-ethyl-2-hydroxybutyric acid, hydroxypentanoic acid, hydroxyhexanoic acid, hydroxyheptanoic acid, hydroxyoctanoic acid, hydroxynonanoic acid, hydroxydecanoic acid and mixtures thereof.

9. The fatty amide as claimed in claim 1 wherein said amide is a diamide according to A) or a triamide according to A) with y/(1−y) varying from 1/20 to 1/2.

10. The fatty amide as claimed in claim 1 wherein said amide is a diamide according to A), with y/(1−y) ranging from 1/10 to 1/2.

11. The fatty amide as claimed in claim 1 wherein said amide is a triamide according to A) with two R2 residues resulting from hydroxylated fatty acid R2CO$_2$H and one resulting from acid R2'CO$_2$H.

12. The fatty amide as claimed in claim 1 which is a diamide represented by option A) according to formula (I).

13. A formulation composition of an organic binder comprising:
a) at least one organic binder,
b) at least one fatty amide as defined in claim 1 as a rheological additive.

14. The composition as claimed in claim 13, wherein said binder a) is selected from: polysiloxane resins terminated by blocked silane groups, polyether resins terminated by blocked silane groups, polysulfide resins terminated by blocked silane groups, polyurethane prepolymer resins terminated by isocyanate groups, polyvinyl chloride (PVC) resins for plastisols, and epoxy resins bearing epoxy groups.

15. The composition as claimed in claim 13, comprising in addition to a) and b) and depending on said binder, a plasticizer or a reactive diluent as defined below:
c) a plasticizer for polysiloxane resins, polyurethane prepolymer resins and PVC resins for plastisols or
d) a reactive diluent from epoxidized monomers for epoxy resins and optionally
e) for two-component systems, a hardener for the epoxy or polyurethane resins.

16. The composition as claimed in claim 15, wherein said organic binder a) is a polysiloxane resin, a polyurethane prepolymer resin or a PVC resin for plastisols and in that said plasticizer is selected from: phthalates, adipates, trimellitates, sebacates, benzoates, citrates, phosphates, epoxides, polyesters, alkylsulfonate esters and non-phthalate substitutes for phthalates.

17. The composition as claimed in claim 16 which is a transparent or non-transparent mastic formulation composition.

* * * * *